United States Patent
Ruijters (10) Patent No.: US 8,764,291 B2
(45) Date of Patent: Jul. 1, 2014

(54) PATIENT TABLE COMPRISING A POSITIONING SYSTEM AND METHOD OF USING SUCH A PATIENT TABLE

(75) Inventor: Daniel Simon Anna Ruijters, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 36 days.

(21) Appl. No.: 13/388,136

(22) PCT Filed: Sep. 28, 2010

(86) PCT No.: PCT/IB2010/054362
§ 371 (c)(1),
(2), (4) Date: Jan. 31, 2012

(87) PCT Pub. No.: WO2011/042832
PCT Pub. Date: Apr. 14, 2011

(65) Prior Publication Data
US 2012/0189095 A1    Jul. 26, 2012

(30) Foreign Application Priority Data
Oct. 6, 2009 (EP) .................................... 09172352

(51) Int. Cl.
*A61B 6/04* (2006.01)
(52) U.S. Cl.
USPC .......................................... 378/209; 378/195

(58) Field of Classification Search
USPC ..................................... 378/208, 209, 20, 195
See application file for complete search history.

(56) References Cited

U.S. PATENT DOCUMENTS

| | | | |
|---|---|---|---|
| 4,589,126 A | 5/1986 | Augustsson et al. | |
| 6,334,708 B1 | 1/2002 | Kosugi | |
| 6,574,808 B1 | 6/2003 | Brown et al. | |
| 7,000,271 B2 * | 2/2006 | Varadharajulu | 5/610 |
| 2005/0084074 A1 | 4/2005 | Varadharajulu | |
| 2006/0104422 A1 | 5/2006 | Iisaku et al. | |
| 2007/0251008 A1 * | 11/2007 | Li | 5/601 |
| 2008/0132780 A1 | 6/2008 | Dewdney | |
| 2010/0008475 A1 * | 1/2010 | Maschke | 5/601 |

FOREIGN PATENT DOCUMENTS

| | | |
|---|---|---|
| DE | 19703556 A1 | 8/1998 |
| FR | 2641180 A1 | 7/1990 |

* cited by examiner

*Primary Examiner* — Hoon Song (57) ABSTRACT

A patient table usable in an X-ray image acquisition arrangement including a table plate connected to a table base via at least one movable joint. The table plate is movable using at least one actuator. To set or re-establish an accurate position/orientation of the movable table plate, the patient table includes a positioning system including a first sensor arrangement for providing position data of the at least one movable joint and a second sensor arrangement for providing position data of the table plate. The accurate position data provided by the second sensor arrangement may be used in a method for improved three-dimensional roadmapping.

16 Claims, 4 Drawing Sheets

PATIENT TABLE COMPRISING A POSITIONING SYSTEM AND METHOD OF USING SUCH A PATIENT TABLE

FIELD OF THE INVENTION

The invention relates to a patient table comprising a positioning system. Furthermore, the invention relates to methods of using such patient table, to an X-ray image acquisition arrangement including such patient table, to a computer program element arranged to control the method of using such patient table and to a computer-readable medium having stored thereon such computer program element.

BACKGROUND OF THE INVENTION

X-ray image acquisition devices have been developed for various clinical applications. By emitting X-rays from an X-ray source towards an object to be examined such as for example a part of a patient and detecting the partially transmitted X-rays on the opposite side of the object, an image of the object showing its interior structure may be acquired due to the differing X-ray absorption properties for example of different types of patient tissue such as bones, muscles, etc.

For example, C-arm systems have been developed which comprise an X-ray source on one end of the C-arm and an X-ray detector on an opposite end of the C-arm. The C-arm may be moved in different directions, in translation direction and/or rotational direction, such that images of the object may be acquired in a large variety of orientations.

In one specific application, a plurality of two-dimensional X-ray images may be acquired under various observation angles and a three-dimensional image may be reconstructed from such plurality of two-dimensional X-ray images. Such three-dimensional image may help for example to visualize a region of interest of a patient to a physician. The three-dimensional image may be displayed to the physician in a screen in different orientations or in different slices. For example, displaying such three-dimensional image may help the physicist during an invasive surgery procedure. During such surgery procedure, additional X-ray images may be acquired and may be compared or overlaid to X-ray images acquired prior to the intervention.

For many clinical applications, it may be important to know the spatial relation between the region of interest within the patient and the acquired X-ray image. For example, in order to be able to easily compare X-ray images acquired prior to an intervention with X-ray images acquired during the intervention, it may be necessary to acquire both types of images at a same position and under a same orientation of the X-ray acquisition device with respect to the region of interest.

One possible application of X-ray imaging during surgery interventions is 3D roadmapping. Therein, a life 2D fluoroscopic image and a 3D reconstruction may be fused into a single visualization. An orientation, position and perspective of 3D data may be matched to a current pose of a C-arm system such that the content of the 2D data and the 3D data overlap. This technique may help to save contrast medium since the 3D reconstructed already shows a vessel volume within a region of interest in the patient. Further, it may increase confidence during the procedure, especially for complex vascular structures where the 3D image clearly shows the vascular morphology.

In order to be able not only to move the X-ray acquisition device such as the C-arm system with respect to a patient but also to be able to move the patient himself for example during a surgery procedure, patient tables have developed which comprise a table plate on which the patient may be stored and which table plate may be moved with respect to a table base fixedly standing on a floor. Advantageously, such patient tables comprise actuators which may be controlled to actively move the table plate with respect to the table base. For example, the table plate may be translated, rotated or tilted with respect to the table base. In order to allow such various movements, the table plate may be connected to the table base via at least one movable joint.

Advantageously, the patient table is adapted to detect an actual position of the table plate by acquiring position data of the at least one movable joint. For example, a position or an angle of a hinge or bearing included in the joint may be measured and the actual position and/or orientation of the table plate may be derived from such position data. Of course, the patient table may comprise more than one movable joint and the position data may be derived from a plurality of measured position values and/or angle values.

Automatic position control systems have been developed allowing storing and recalling a pose of a geometrical arrangement. It is available for both, the C-arm and the patient table geometry. Conventionally, this may be done by storing a mechanical position of the one or more joint(s) included in the C-arm system and the patient table, respectively.

However, it has been observed that using conventional automatic position control systems may not always result in satisfying positioning results.

SUMMARY OF THE INVENTION

Accordingly, there may be a need for an X-ray image acquisition arrangement and a method of using such arrangement in which a positioning of a region of interest with respect to an X-ray image acquisition device may be reliably improved.

Such need may be met by a patient table, a method of using such patient table, an X-ray image acquisition arrangement, a computer program element and a computer-readable medium according to the appended independent claims. Advantageous embodiments are defined in the dependent claims.

Aspects and embodiments of the present invention have been developed based on the following finding: In many X-ray image acquisition procedures, a spatial relation between an X-ray source and a detector mounted for example on a C-arm system and a world coordinate system may be well established by means of measuring mechanical angles and calibrations. However, a relation between the world coordinate system and the table plate of a patient table on which a patient to be examined may be stored may be more difficult to establish, due to for example an irreproducible behaviour of a patient table's positioning system. Such irreproducible behaviour may be caused for example by differences in weight distribution on the table plate for example as a result of a movement of the patient during the procedure or as a result of a surgeon resting on the table plate during the procedure. Accordingly, it has been observed that although a patient table has been commanded to e.g. re-establish a specific positioning of the table plate identical to a positioning of the table plate during a previous image acquisition procedure by commanding the actuators of the patient table to re-establish the same mechanical angles/positions of the movable joint(s), a position of the table plate actually realized may differ from the position of the table plate during the previous image acquisition procedure. Accordingly, it may be difficult to compare X-ray images acquired during the previous and the later image acquisition. Or, in the example of 3D roadmapping, actually acquired 2D X-ray images may not satisfyingly overlap with a previously reconstructed 3D image.

According to a first aspect of the invention, a patient table comprising a positioning system is proposed. Therein, the patient table comprises a table plate being connected to a table base via at least one movable joint wherein the table plate is movable using at least one actuator. The positioning system comprises a first sensor arrangement for providing position data of the at least one movable joint. Furthermore, the positioning system comprises a second sensor arrangement for providing position data of the table plate.

According to a second aspect of the invention, a method of using the patient table according to the first aspect is proposed. The method is used for automatically positioning the patient table and comprises the following steps:

a) acquiring original first position data of the at least one movable joint using the first sensor arrangement;
b) acquiring original second position data of table plate using the second sensor arrangement;
c) moving the table plate to a different position;
d) moving the table plate by controlling the actuator based on the first position data;
e) acquiring actual second position data of the table plate using the second sensor arrangement;
f) moving the table plate by controlling the actuator based on a difference between the original second position data and the actual second position data; and
g) iteratively repeating steps (e) and (f) until a difference between the original second position data and the actual second position data is below a threshold value.

According to a third aspect of the invention, a further method of using a patient table according to the above first aspect is proposed. This method may be used for three-dimensional roadmapping and comprises the following steps, preferably in the indicated order:

a) acquiring a three-dimensional X-ray image of an object positioned on the patient table and acquiring original first position data of the at least one movable joint using the first sensor arrangement and acquiring original second position data of the table plate using the second sensor arrangement;
b) moving the table plate to a different position;
c) acquiring a two-dimensional X-ray image of the object positioned on the patient table and acquiring actual second position data of the at least one marker using the second sensor arrangement;
d) transforming the three-dimensional X-ray image based on a difference between the original second position data and the actual second position data; and
e) overlaying the transformed three-dimensional X-ray image and the acquired two-dimensional X-ray image.

The methods of the second or third aspect may be implemented in a patient table or an X-ray image acquisition arrangement in order to improve re-positioning capabilities or three-dimensional roadmapping capabilities, respectively.

According to a fourth aspect of the invention, a computer program element being configured and arranged to control a method according to the second or third aspect when executed on a computer is proposed.

According to a fifth aspect of the invention, a computer-readable medium having stored thereon the computer program element according to the fourth aspect is proposed.

Aspects of the present invention may be seen as based on the following idea:

As it has been observed that a patient table comprising a positioning system controlling a positioning of a table plate only on position data of the movable joint(s) connecting the table plate with the table base may not provide for sufficient positioning accuracy, it is proposed to add a second sensor arrangement to the positioning system. This second sensor arrangement is adapted for providing position data of the patient table itself or of at least one marker attached to the patient table.

It is to be emphasized that the second sensor arrangement does not replace the first sensor arrangement but supplements the positioning system. In other words, the positioning system comprises two separate sensor arrangements operating based on different measuring principles, i.e. the first sensor arrangement may be adapted to determine the position of the table plate by measuring a position/orientation status of the movable joint(s) and the second sensor arrangement may determine a position of the table plate by measuring a position/orientation of e.g. one or more markers which markers may be arranged at the table plate.

It has been found that each of the first and second sensor arrangements may have its own advantages and deficiencies and that a positioning system comprising such two different sensor arrangements may allow improved positioning characteristics such as an improved positioning accuracy and/or an improved positioning robustness.

For example, the first sensor arrangement may rely on mechanical position measurements relating to the movable joint(s). Therefore, the first sensor arrangement may measure a position of the table plate over a large motion range. Furthermore, the first sensor arrangement can be directly coupled to a control for the actuator such that control data driving the actuator may be used for providing the position data. On the other hand, the second sensor arrangement may be adapted for measuring a position of the patient table with an accuracy higher than the measuring accuracy of the first sensor arrangement. Particularly, the marker(s) may be attached to the table plate at a position close to the expected region of interest such that the position data provided by the second sensor arrangement closely correspond to the actual position of the region of interest.

The second sensor arrangement may be adapted for non-mechanically measuring, i.e. for example optically measuring, a position of the table plate or particularly of the at least one marker arranged at the table plate. Due to such non-mechanical/optical measuring capability, a high measuring accuracy may be achieved. The position of the marker(s) may be measured absolutely in space, i.e. in a world coordinate system, preferably independent of any mechanical influences such as for example bending of components of the patient table due to additional loads exerted thereon.

The second sensor arrangement may comprise at least one camera provided on the table base. The camera may be oriented such that its field of view is directed to the expected position of the marker(s). In such embodiment, preferably at least three markers are attached to the table plate of the patient table in fixed positions relative to each other. From an image of the at least three markers acquired by the camera and taking into account the known position of the camera at the table base, a precise position and orientation of the patient table may be determined.

The method according to the second aspect of the invention may benefit from the improved positioning characteristics of the patient table according to the first aspect of the invention. The method may be used to acquire original position data with respect to an initial position of the table plate and to then, at a later stage in time and after the table plate has been moved to a different position, to re-establish the original position with high position/orientation accuracy. For such purpose, the positioning system not only acquires original first position data relating to a position/orientation status of the movable joint(s) but also acquires precise original second position data relating to a position of the table plate itself or of the marker(s) arranged at the table plate. At the later point in time, the table plate of the patient table may first be moved towards the original position by controlling the actuator based on the original first position data. However, such positioning of the table plate may not be accurate enough. Therefore, actual second position data of the marker(s) are acquired using the second sensor arrangement and the table plate of the patient table is moved towards the original position by controlling the actuator based on a difference between the original second position data and the actual second position data. This process of acquiring actual second position data and then moving the table plate based on a deviation to the original second position data may be iteratively repeated until the difference is below a threshold value wherein the threshold value indicates a positioning accuracy to be achieved.

The proposed positioning method may be implemented into the patient table according to the first aspect of the invention by suitably adapting a control device comprised in the patient table. Thereby, an automatic positioning control may be implemented with a high positioning accuracy and a high robustness. For example, while the moving of the table plate by controlling the actuator based on the first position data may be fast, robust, easy to implement, independent of any defects of the second sensor arrangement, etc., the subsequent moving of the table plate by controlling the actuator based on a difference between the original second position data and the actual second position data may allow for a very high positioning accuracy, preferably independent of any mechanical influence.

The method for three-dimensional roadmapping according to the third aspect of the invention may benefit from the characteristics of the patient table of the first aspect of the invention in that a three-dimensional X-ray image may be acquired at a first point in time wherein the position of the table plate may be precisely recorded acquiring original position data using both, the first and second sensor arrangements, and that then, at a later second point in time and after having moved the table plate to a different position, the table plate may be moved towards the original position by controlling the actuator based on the original first position data and then acquiring one or more current two-dimensional X-ray image (s) of the object positioned on the table plate. Such current two-dimensional X-ray image(s) may be overlaid/superimposed with the originally acquired three-dimensional X-ray image in order to provide three-dimensional roadmapping for a physician. However, as the actual position of the table plate may still differ from the original position of the table plate, actual second position data of the at least one marker are acquired using the second sensor arrangement. These actual second position data may be acquired with high accuracy and may be independent of any mechanical influence onto the table plate. Based on a difference between the actual second position data and the original second position data, the three-dimensional X-ray image may be re-positioned and/or re-oriented such that an improved overlay of the transformed three-dimensional X-ray image and the currently acquired two-dimensional X-ray image(s) may be achieved.

The method according to the third aspect of the invention may be implemented in an X-ray image acquisition arrangement comprising an X-ray image acquisition device such as a C-arm system including an X-ray source and an X-ray detector. Additionally, the X-ray image acquisition arrangement comprises a patient table as defined with respect to the first aspect of the invention and a control device being adapted to control the patient table for performing the method as defined with respect to the third aspect of the invention. Using such X-ray image acquisition arrangement allows an improved 3D roadmap being essentially independent of any mechanical influence onto the table plate.

It has to be noted that aspects and embodiments of the present invention have been described with reference to different subject-matters. In particular, some aspects and embodiments have been described with reference to method type claims whereas other embodiments have been described with reference to apparatus type claims. However, a person skilled in the art will gather from the above and the following description that, unless other notified, in addition to any combination of features belonging to one type of subject-matter also any combination between features relating to different subject-matters, in particular between features of the apparatus type claims and features of the method type claim, is considered to be disclosed with this application.

BRIEF DESCRIPTION OF THE DRAWINGS

Features and advantages of the present invention will be further described with respect to specific embodiments as shown in the accompanying figures but to which the invention shall not be limited.

Features shown in the drawings are schematic and not to scale.

DETAILED DESCRIPTION OF EMBODIMENTS

Figure 1:
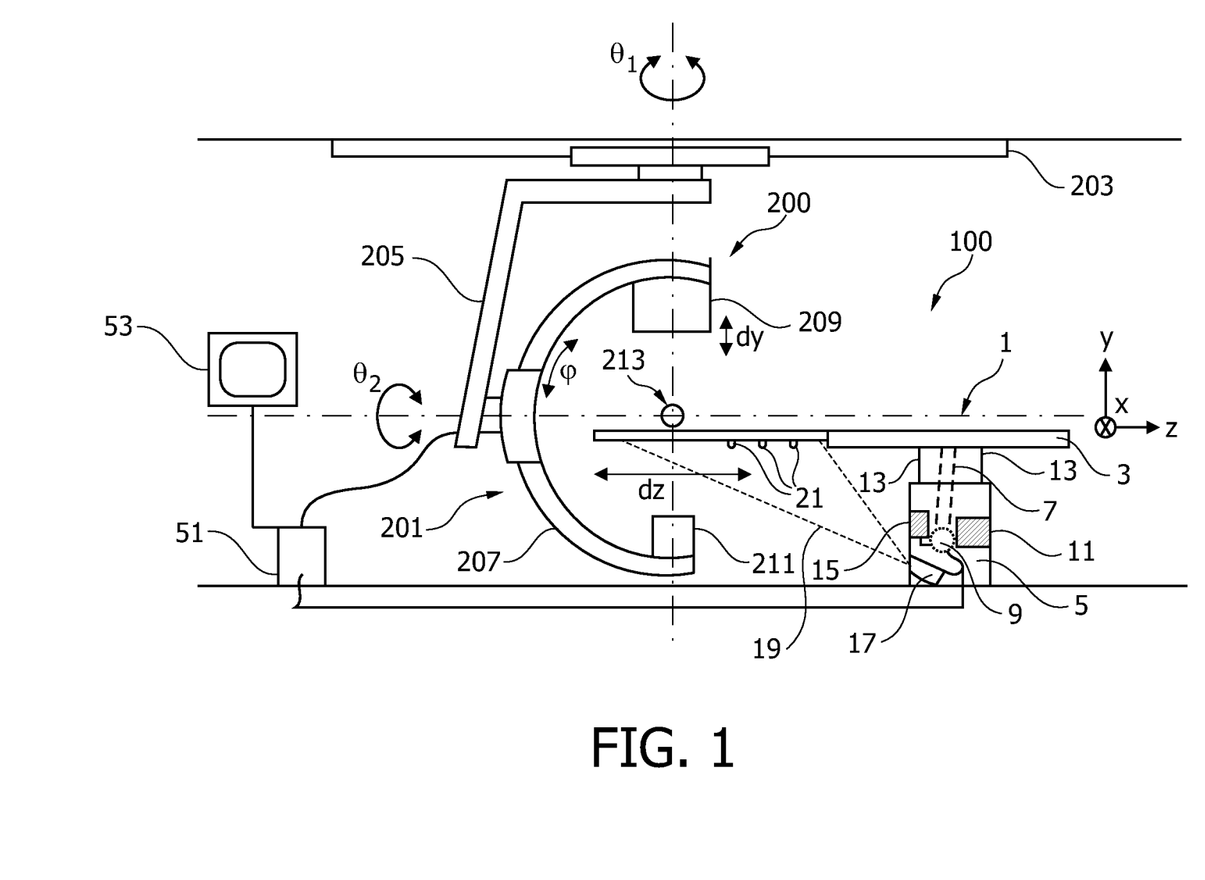
FIG. 1 shows an X-ray image acquisition arrangement comprising a patient table according to an embodiment of the present invention.
Figure 2:
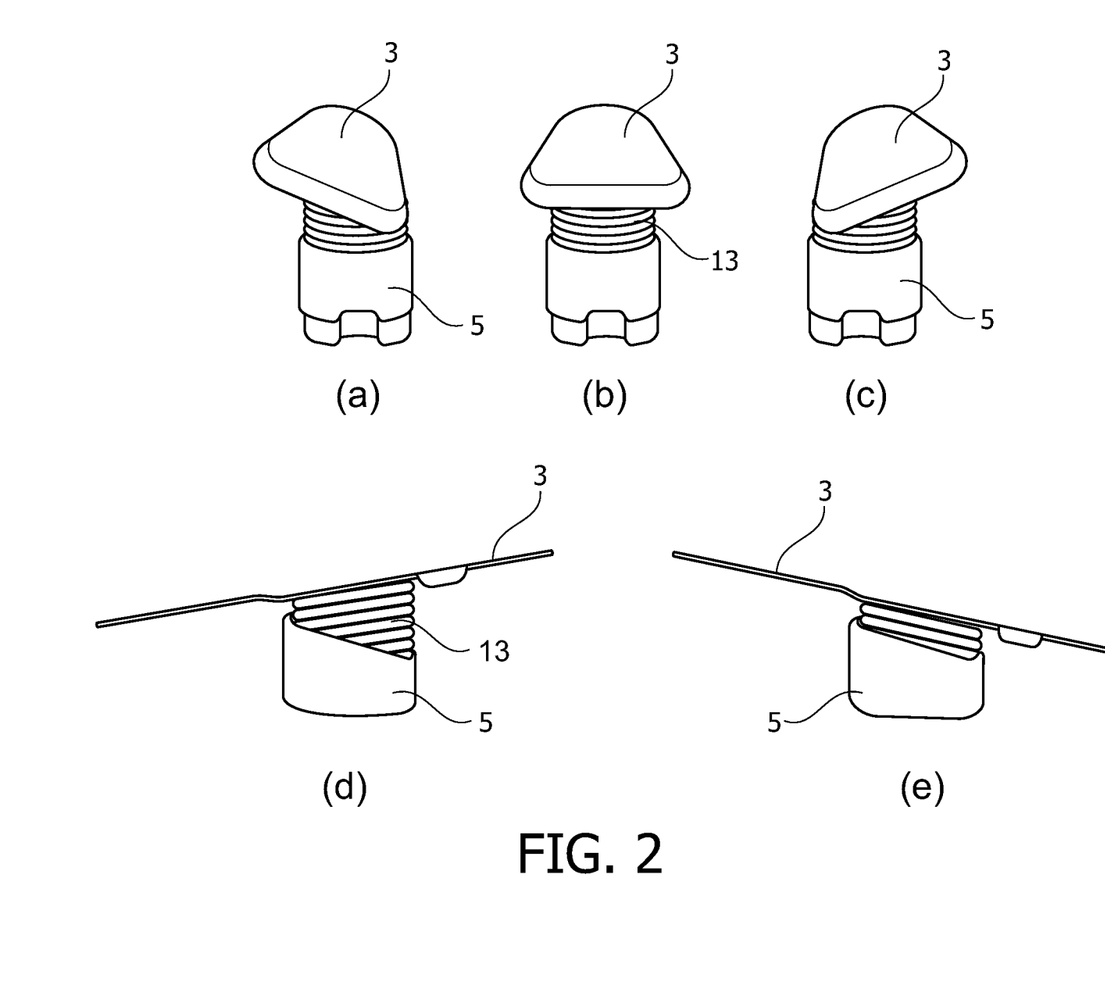
FIG. 2 illustrates possible motions of a table plate of a patient table according to an embodiment of the present invention.

FIG. 1 shows an X-ray image acquisition arrangement 100 comprising an X-ray image acquisition device 200 and a patient table 1. The X-ray image acquisition device 200 comprises a C-arm system 201 being attached to a ceiling 203 via a movable attachment mechanism 205. The C-arm system 201 comprises a C-arm 207. On one end of the C-arm 207, an X-ray source 209 is attached. At an opposite end of the C-arm 207, an X-ray detector 211 is arranged. The C-arm system 201 may be moved translationally and rotationally along different directions or about different axes as indicated in FIG. 1 by respective arrows in order to move the C-arm along various degrees of freedom, i.e. L-arm, propeller, roll, source-imaging-distance (SID), etc. Such capability for various motions of the C-arm 207 allows to position the X-ray source 209 and the X-ray detector 211 such that X-ray images of a region of interest 213 within a patient lying on the patient table 1 can be acquired (for clarity reasons, the patient is not shown in FIG. 1).

The patient table 1 comprises a table plate 3 and a table base 5. The table plate 3 is connected to the table base 5 via a lever 7 attached to a movable joint 9. An actuator 11 is provided for moving the table plate 3. A collar 13 is arranged between the table plate 3 and the table base 5 in order to cover the lever 7. A first sensor arrangement 15 is provided for acquiring position data indicating a position and/or orientation of the movable joint 9. Such position data at least roughly relate to a position of the table plate 3 connected to the movable joint 9 via the lever 7.

It is to be noted that the moving mechanism in FIG. 1 including the actuator 11, the lever 7 and the movable joint 9 as well as the first sensor arrangement 15 shown in FIG. 1 are illustrated and described in a very simplified manner. One skilled in the art may clearly realize various possibilities of embodying the respective components of the patient table 1. For example, the actuator 11 may include one or more motors adapted for directly or indirectly applying a force to the table plate 3 or the lever 7 or the joint 9 attached thereto. Furthermore, instead of a single movable joint 9 and a single lever 7, a more complicated mechanism including a plurality of joints and levers may be provided. Furthermore, the first sensor arrangement 15 may be realized in various manners. For example, the first sensor arrangement may be adapted for detecting a displacement or a rotation of one or more components of the actuating mechanism. Although the first sensor arrangement 15 is shown as a separate part in FIG. 1, it may also be integrated in one of the components of the actuating mechanism. For example, the first sensor arrangement may be integrated into the actuator 11 such that for example a motor included in the actuator 11 provides a feedback on a motion induced by the actuator thereby providing position data with respect to the joint 9.

In the table base 5, a second sensor arrangement 17 is integrated. This second sensor arrangement 17 comprises a camera which is positioned and oriented such that its field of view 19 includes a portion of the table plate 3 at which three markers 21 are provided. The three markers 21 are arranged in a triangle. By acquiring an image of the markers 21 using the camera, the second sensor arrangement may provide position data of the markers 21 as the fixed position of the markers 21 with respect to each other as well as the fixed position of the camera included in the second sensor arrangement 17 are known. Accordingly, a position of an area of the table plate 3 to which the markers 21 are fixedly attached may be determined by the second sensor arrangement optically and with high accuracy.

It has to be noted that the position, the number and the distance of the markers 21 with respect to each other may vary. As well, the position, orientation and number of cameras may vary. As shown in FIG. 1, a single camera can be used for the second sensor arrangement 17. Then, at least three markers 21 should be provided on the table plate 3. The position of the markers 21 may then be established by using the fact that their relative position is always fixed. Due to the perspective the lines through the markers and the focal spot of the camera their position in world coordinates can be uniquely determined.

It is possible to optionally add multiple cameras in order to increase the accuracy and/or to be robust against occlusion of markers 21. It is also possible to add multiple markers 21 in a unique pattern to be robust against occlusions of some markers and to be less dependent on the field of view of the camera(s).

Alternatively, it is possible to determine the position of the markers by using stereo cameras. For this approach, at least one marker 21 should be used for determining the position, and at least two markers should be used for determining the orientation of the table plate 3. Of course, also here it is possible to optionally add more cameras and/or markers to improve accuracy and/or to be robust against occlusion of markers.

Both, the image acquisition device 200 and the patient table 1 are connected to a control device 51. The control device 51 may be adapted to acquire position data of the patient table 1 as well as position data of the image acquisition device 200. Furthermore, the control device 51 may acquire image data provided by the X-ray detector 211. As will be described in further detail below, using such data an image of the region of interest 213 may be displayed on a display 53 connected to the control device 51. Furthermore, a superposition of a previously acquired three-dimensional image of the region of interest 213 and a current two-dimensional image acquired by the image acquiring device 200 may be displayed on the display 53 for X-ray roadmapping.

FIG. 2(a)-(e) illustrates various motion capabilities of the table plate 3 with respect to the table base 5 of a patient table 1. The table plate 3 may be displaced and/or tilted with respect to table base 5. The collar 13 encloses and protects the actuation mechanism including the joint 9 and the lever 7 connecting the table plate 3 to the table base 5.

Figure 3:
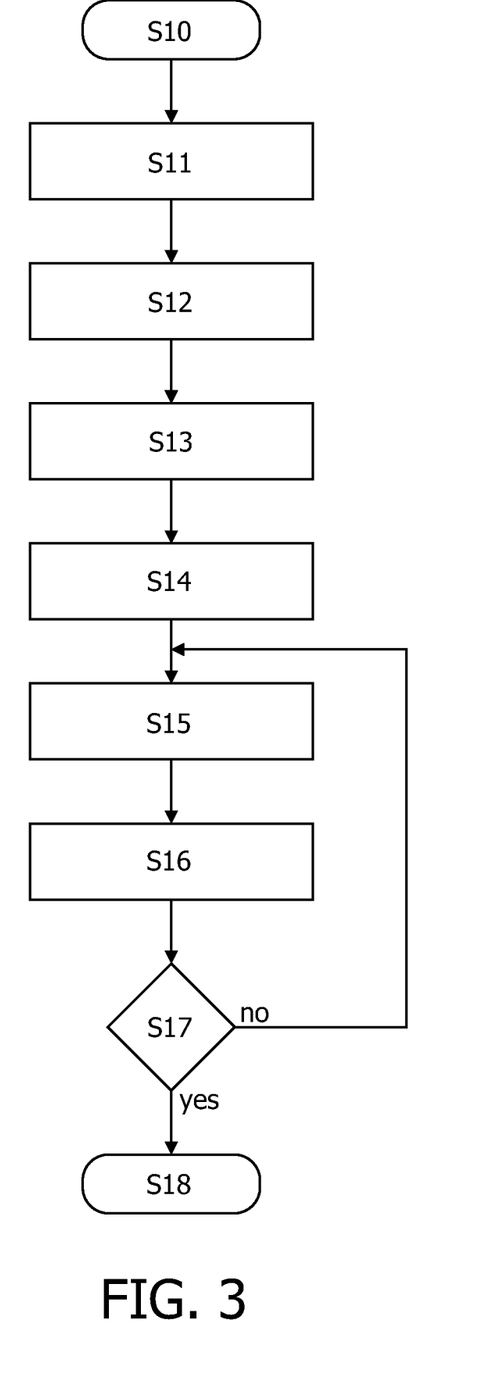
FIG. 3 shows a flow-chart of a method for automatically positioning a patient table according to an embodiment of the present invention.

With respect to the flow-chart shown in FIG. 3, a method of using a patient table 1 for automatically positioning the table plate 3 is described.

After having started a procedure (step S10) original first position data of the at least one movable joint 9 are acquired using the first sensor arrangement 15 (step S11). Then, original second position data of the at least one marker 21 are acquired using the second sensor arrangement 17 (step S12).

It is to be noted that the steps of acquiring the first and second original position data may be performed sequentially or simultaneously and that the order of acquiring such position data generally does not matter.

Together with the acquisition of the original first and second position data, further processing steps may be performed in a first stage in time. For example, a set of X-ray images may be acquired using an X-ray image acquisition device 200. The original first and second position data may then indicate a positional relationship between a region of interest of a patient stored on the patient table and the X-ray image acquisition device used for acquiring the X-ray images.

After such process steps S11, S12 being performed at a first stage in time, the table plate 3 may be moved to a different position (step S13). For example, the patient table 1 may be used for different purposes such as for example acquiring X-ray images of a different region of interest.

Then, at a second later stage in time, the patient table 1 may be used for example for acquiring X-ray images of the same region of interest of the same patient again. For such purposes, it may be necessary to restore the original position of the table plate 3 with high accuracy. Therefore, the table plate 3 is first moved by controlling the actuator 11 based on the original first position data (step S14). In other words, the actuator 11 is controlled so as to restore the original position/orientation of the movable joint 9 as in the first stage in time.

However, as it has been observed that such restoring of the position based only on the original first position data may not always result in the region of interest being exactly at the same position/orientation as during the first stage in time possibly due to mechanical loads acting onto the patient table, additional positioning steps are performed.

First, actual second position data of the at least one marker 21 are acquired using the second sensor arrangement 17 (step S15). The actual second position data accurately indicate the actual position/orientation of the area of the table plate 3 to which the marker(s) is/are attached.

Then, the table plate 3 is moved by controlling the actuator 11 based on a difference between the original second position data and the actual second position data (step S16). In other words, the actual second position data indicating the actual position and orientation of the marker(s) 21 during the second stage in time is compared with the original second position data indicating the position and orientation of the marker(s) during the first stage in time and the table plate 3 is moved in accordance with a difference between such original and actual position data.

Such re-adjusting of the position and orientation of the table plate 3 is performed iteratively, i.e. the steps S15 and S16 are repeated until in a decision step S17 it is determined that the difference between the original second position data and the actual second position data is below a threshold value.

In other words, the differences in position $\delta_{pos}$ and the differences in orientation $\delta_{orient}$ may be minimized with $$\delta_{pos} = \mu \|\vec{P}_{original} - \vec{P}_{actual}\|$$

$$\delta_{orient} = \angle(\vec{r}_{original}, \vec{r}_{actual})$$

Therein $\vec{p}$ denotes the (average) position of the marker(s) in world coordinates and $\vec{r}$ denotes the orientation of the marker configuration in world coordinates. It may be clear that and $\delta_{pos}$ and $\delta_{orient}$ may be functions of the mechanical parameters of the patient table. The controlling system may be set up with a PID controller or a Kalman filter for example.

After the position and orientation of the patient table 3 has been restored in such processing sequence S15, S16, S17 iteratively, a deviation in position and orientation of the patient table 3 between the first stage in time and the second stage in time is smaller than the given threshold. Accordingly, the accuracy of the re-positioning process may be determined by correspondingly selecting the threshold value. The re-positioning procedure may then end at step S18.

Having re-established the original position with high accuracy, X-ray images may be acquired for example during the second stage in time which X-ray images accurately correspond to the X-ray images acquired in the first stage in time concerning a position/orientation relation between the region of interest and the X-ray image acquiring device. Therefore, the actual X-ray images can be easily compared or overlaid with the original X-ray images.

Figure 4:
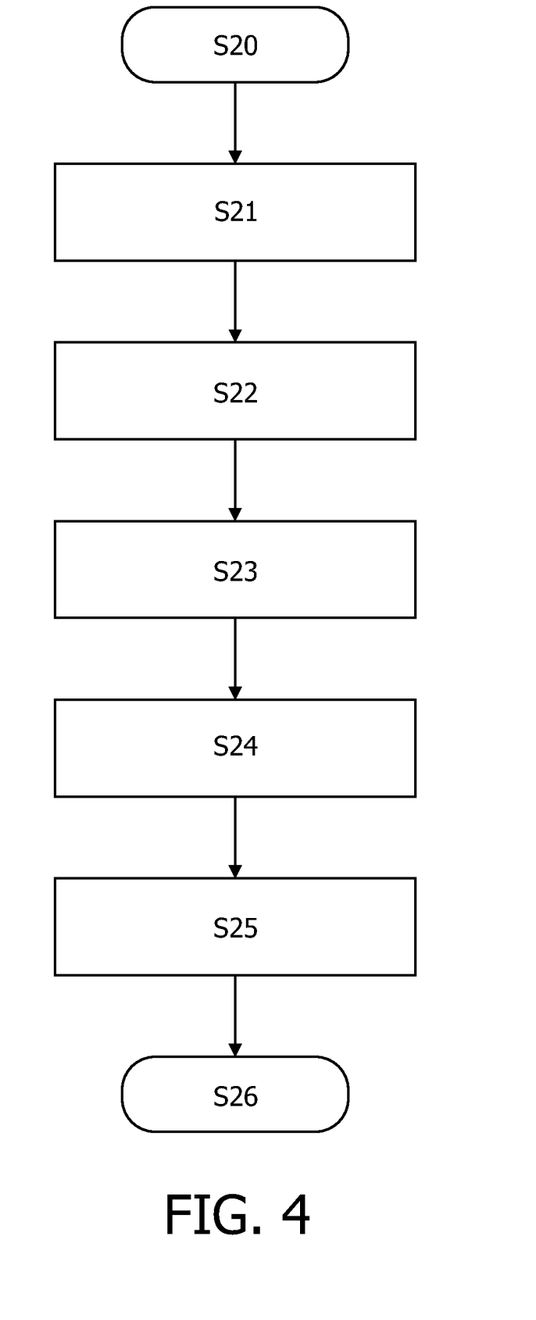
FIG. 4 shows a flow-chart of a method for three-dimensional roadmapping using a patient table according to an embodiment of the present invention.

With respect to FIG. 4, an embodiment of a method of using the patient table for three-dimensional roadmapping will be explained.

After having started the procedure (step S20), in a first step S21, a plurality of two-dimensional X-ray images of a region of interest of a patient positioned on the patient table 3 is acquired under various acquisition angles. From such plurality of two-dimensional X-ray images, a three-dimensional X-ray image may be provided. For example, such three-dimensional X-ray image may provide a detailed representation of a vascular system within the region of interest of the patient. At this first stage in time, original first position data of the at least one movable joint 9 are acquired using the first sensor arrangement 15 and original second position data of the at least one marker 21 are acquired using the second sensor arrangement 17. The various image acquisitions and position data acquisitions may be performed simultaneously or in an arbitrary sequential order.

Before using the patient table 1 for 3D Roadmapping, it may be used for different purposes and the table plate 3 may be moved to a different position (step S22).

Then at a second stage in time, at least one two-dimensional X-ray image of the region of interest of the patient positioned on the table plate 3 is acquired. Together therewith or subsequent thereto, actual second position data of the at least one marker 21 are acquired using the second sensor arrangement 17 (step S23).

A deviation between the position and orientation of the region of interest during the first stage in time and during the second stage in time may be indicated by a difference between the original second position data and the actual second position data. In other words, a translation deviation $\vec{t}$ and a rotation deviation $\phi$ may be expressed as $$\vec{t} = \vec{p}_{original} - \vec{p}_{actual}$$

$\phi = \arcsin(<\vec{r}_{original}, \vec{r}_{actual}>)$ wherein $<>$ denotes the in-product, around axis $\vec{a} = \vec{r}_{original} \times \vec{r}_{actual}$ Based on the difference between the original second position data and the actual second position data, the originally acquired three-dimensional X-ray image is transformed (step S24) and then overlaid to the actually acquired two-dimensional X-ray image (step S25) before terminating the procedure (step S26).

By transforming the originally acquired three-dimensional X-ray image in such a way, deviations between the position and orientation during the first stage in time and during the second stage in time may be compensated such that the original three-dimensional X-ray image may be accurately overlaid with the actually acquired two-dimensional X-ray image for three-dimensional roadmapping purposes.

It should be noted that terms such as "comprising" do not exclude other elements or steps and that the indefinite article "a" does not exclude a plurality. Also elements described in association with different embodiments may be combined. It should also be noted that reference signs in the claims shall not be construed as limiting the scope of the claims.

LIST OF REFERENCE SIGNS

1 Patient table
3 Table plate
5 Table base
7 Lever
9 Joint
11 Actuator
13 Collar
15 First sensor arrangement
17 Second sensor arrangement
19 Field of view
51 Control device
53 Display
100 X-ray image acquisition arrangement
200 X-ray image acquisition device
201 C-arm system
203 Ceiling
205 Attachment mechanism
207 C-arm
209 X-ray source
211 X-ray detector
213 Region of interest

The invention claimed is:

1. A patient table comprising a positioning system,
   wherein the patient table comprises a table plate being connected to a table base via at least one movable joint wherein the table plate is movable using at least one actuator;
   wherein the positioning system comprises:
      markers attached to the table plate;
      a first sensor arrangement for providing position data of the at least one movable joint; and
      a second sensor arrangement wherein at least one sensor of the second sensor arrangement is configured to provide position data of the table plate by detecting a position of at least two of the markers,
wherein the second sensor arrangement comprises at least one camera provided on the table base for detecting the position of the at least two of the markers.

2. The patient table of claim 1, wherein the second sensor arrangement is adapted for non-mechanically measuring a position of the table plate.

3. The patient table of claim 1, wherein the second sensor arrangement is adapted for optically measuring a position of the table plate.

4. The patient table of claim 1, wherein the second sensor arrangement is adapted for providing position data of the markers.

5. The patient table of claim 4, wherein at least three markers are attached to the table plate in fixed positions to each other and the sensor arrangement is configured to provide a perspective position of the markers to each other for providing the position data of the table plate.

6. The patient table of claim 1, wherein the second sensor arrangement is adapted for measuring a position of the table plate with an accuracy higher than a measuring accuracy of the first sensor arrangement.

7. The patient table of claim 1, further comprising a control device being adapted to control the patient table.

8. An X-ray image acquisition arrangement, comprising:
an X-ray image acquisition device comprising an X-ray source and an X-ray detector; the patient table of claim 1,
a control device being configured to control the patient table.

9. The X-ray image acquisition arrangement of claim 8, wherein the control device is configured to:
acquire a 3-dimensional X-ray image of an object positioned on the table plate, acquire original first position data of the at least one movable joint using the first sensor arrangement, and acquire original second position data of the table plate using the second sensor arrangement;
move the table plate to a different position;
acquire a 2-dimensional X-ray image of the object positioned on the table plate and acquire actual second position data of the table plate using the second sensor arrangement;
transform the 3-dimensional X-ray image based on a difference between the original second position data and the actual second position data; and
overlay the transformed 3-dimensional X-ray image and the acquired 2-dimensional X-ray image.

10. A method of using a patient table for automatically positioning a table plate of the patient table connected to a table base via at least one movable joint wherein the table plate is movable using at least one actuator, the method comprising acts of:
(a) acquiring original first position data of the at least one movable joint using a first sensor arrangement;
(b) acquiring original second position data of the table plate using a second sensor arrangement by detecting a position of at least two markers attached to the table plate;
(c) moving the table plate to a different position;
(d) moving the table plate by controlling the actuator based on the original first position data;
(e) acquiring actual second position data of the table plate using the second sensor arrangement;
(f) moving the table plate by controlling the actuator based on a difference between the original second position data and the actual second position data;
(g) iteratively repeating steps (e) and (f) until a difference between the original second position data and the actual second position data is below a threshold value.

11. A program element configured and arranged to control when executed on a computer the method of claim 10.

12. A computer readable medium having stored thereon the program element according to claim 11.

13. A method of using a patient table including a table plate that is movable by at least one movable joint for 3-dimensional roadmapping, the method comprising acts of:
(a) acquiring a 3-dimensional X-ray image of an object positioned on the table plate and acquiring original first position data of the at least one movable joint using a first sensor arrangement and acquiring original second position data of the table plate using a second sensor arrangement;
(b) moving the table plate to a different position;
(c) acquiring a 2-dimensional X-ray image of the object positioned on the table plate and acquiring actual second position data of the table plate using the second sensor arrangement;
(d) transforming the 3-dimensional X-ray image based on a difference between the original second position data and the actual second position data;
(e) overlaying the transformed 3-dimensional X-ray image and the acquired 2-dimensional X-ray image.

14. A program element configured and arranged to control when executed on a computer the method of claim 13.

15. A computer readable medium having stored thereon the program element according to claim 14.

16. A control device for an X-ray image acquisition arrangement comprising an X-ray source, an X-ray detector, a patient table including a table plate connected to a table base via at least one movable joint and movable using at least one actuator, a first sensor arrangement for providing position data of the at least one movable join, and a second sensor arrangement for providing position data of the table plate, the control device being configured to:
acquire a 3-dimensional X-ray image of an object positioned on the table plate at an original position;
acquire original first position data of the at least one movable joint using the first sensor arrangement;
acquire original second position data of the table plate using the second sensor arrangement;
move the table plate to a second position;
acquire a 2-dimensional X-ray image of the object positioned on the table plate;
acquire actual second position data of the table plate using the second sensor arrangement;
transform the 3-dimensional X-ray image based on a difference between the original second position data and the actual second position data; and
overlay the transformed 3-dimensional X-ray image and the acquired 2-dimensional X-ray image.

* * * * *